(12) United States Patent
Akashi et al.

(10) Patent No.: US 8,835,570 B2
(45) Date of Patent: Sep. 16, 2014

(54) HYDROPHILIC MATERIAL, MEDICAL MATERIAL AND SUSTAINED DRUG RELEASE MATERIAL

(75) Inventors: Mitsuru Akashi, Osaka (JP); Michiya Matsusaki, Osaka (JP); Dongjian Shi, Jiangsu (CN); Makoto Onishi, Kanagawa (JP); Yotaro Fujita, Shizuoka (JP)

(73) Assignees: Osaka University, Osaka (JP); Terumo Kabushiki Kaisha, Tokyo (JP)

( * ) Notice: Subject to any disclaimer, the term of this patent is extended or adjusted under 35 U.S.C. 154(b) by 322 days.

(21) Appl. No.: 13/121,604

(22) PCT Filed: Sep. 29, 2009

(86) PCT No.: PCT/JP2009/066966
§ 371 (c)(1),
(2), (4) Date: Apr. 29, 2011

(87) PCT Pub. No.: WO2010/038747
PCT Pub. Date: Apr. 8, 2010

(65) Prior Publication Data
US 2011/0257338 A1    Oct. 20, 2011

(30) Foreign Application Priority Data

Sep. 30, 2008  (JP) ................................ 2008-253053

(51) Int. Cl.
*C08G 63/664* (2006.01)
*C08G 63/91* (2006.01)
*A61K 9/51* (2006.01)

(52) U.S. Cl.
CPC ............ *C08G 63/912* (2013.01); *C08G 63/664* (2013.01); *A61K 9/5153* (2013.01)
USPC ....................................... 525/450; 525/329.8

(58) Field of Classification Search
CPC ............................. C08G 63/664; C08G 63/912
USPC .............................................. 525/329.8, 450
See application file for complete search history.

(56) References Cited

U.S. PATENT DOCUMENTS

| | | | |
|---|---|---|---|
| 4,053,415 A | 10/1977 | Satomura | |
| 4,355,136 A | 10/1982 | Dombroski et al. | |
| 4,874,540 A * | 10/1989 | Greenwald et al. | ......... 510/476 |
| 6,958,212 B1 * | 10/2005 | Hubbell et al. | ......... 424/78.17 |
| 7,182,884 B2 | 2/2007 | Kaneko et al. | |

FOREIGN PATENT DOCUMENTS

| | | |
|---|---|---|
| EP | 1 873 183 A1 | 1/2008 |
| JP | 50-21804 A | 3/1975 |
| JP | 60-110722 A | 6/1985 |
| JP | 11-60928 A | 3/1999 |
| JP | 2004-250700 A | 9/2004 |
| WO | WO 0145758 A1 * | 6/2001 |
| WO | WO 2007084126 A1 * | 7/2007 |
| WO | WO 2009/054113 A1 | 4/2009 |

OTHER PUBLICATIONS

Shi, et al., "Particulation of Hyperbranched Aromatic Biopolyesters Self-Organized by Solvent Transformation in Ionic Liquids", Mar. 27, 2007, Langmuir, 23(7), 3485-3488.*
Notification of Transmittal of Translation of the International Preliminary Report on Patentability (Form PCT/IB/338), International Preliminary Report on Patentability (Form PCT/IB/373), Written Opinion of the International Search Authority (Form PCT/ISA/237) mailed in corresponding International Patent Application No. PCT/JP2009/066966, May 19, 2011, The International Bureau of WIPO, Geneva, CH.
Mitsuru Akashi, "Kankyojunkangata Enjiniaringupurasuchikku (environmentally recyclable engineering plastics)," Kobunshi (High Polymers, Japan), the organ of the Society of Polymer Science, Japan, vol. 55, No. 11, p. 870-873. 2006 (month unknown), and its partial translation.
International Search Report (PCT/ISA/210) issued on Dec. 28, 2009, by Japanese Patent Office as the International Searching Authority for International Application No. PCT/JP2009/066966.
Extended European Search Report dated Sep. 9, 2013, issued in corresponding European Patent Application No. 09817779.3.
Mather et al., "Michael addition reactions in macromolecular design for emerging technologies," Progress in Polymer Science, Pergamon Press, Oxford, GB, vol. 31, No. 5, May 1, 2006, pp. 487-531.

* cited by examiner

*Primary Examiner* — Mark Kaucher
(74) *Attorney, Agent, or Firm* — Buchanan Ingersoll & Rooney PC (57) ABSTRACT

A hydrophilic material having a hydrophilic nature and being biocompatible and processable into nanoparticles wherein a hydrophilic monomer such as threitol or a hydrophilic polymer such as polyethylene glycol is attached to the β position of an α,β-unsaturated carboxyl group of a (co)polymer comprising an aromatic compound such as 4-hydroxycinnamic acid in which an aromatic ring is substituted by the α,β-unsaturated carboxyl group and one or more hydroxyl groups. In particular, a hydrophilic material having a nanoparticle size which is highly dispersible in water, can well migrate into the blood and is useful as a drug carrier, a medical material and a sustained drug release material.

8 Claims, 8 Drawing Sheets

BEFORE CARRYING BSA

FIG. 8C

AFTER CARRYING BSA

HYDROPHILIC MATERIAL, MEDICAL MATERIAL AND SUSTAINED DRUG RELEASE MATERIAL

TECHNICAL FIELD

The present invention relates to hydrophilic materials, medical material, and sustained drug release material.

BACKGROUND ART

Plastics has developed along with the progress of chemistry and, as being highly functional materials used in every field as a substitute for metal, belongs to the indispensable materials of today. Plastics finds settled application as industrial materials in commodities and various other products, and the range of applications thereof is being widely enlarged, from nuclear power-related uses to space and ocean developments. Plastics is the materials which are possessed of prominent properties and potentials unique to other materials, and is characterized by a reduced weight, moldability, capability to be formed into a product of complicated shape in fewer steps, a high corrosion resistance, an improved resistance to chemical attack, and so forth. While the heat resistance of plastics used to be poor as compared with metal, design and development of a novel, heat-resistant polymeric material took off in the 1960s, and polymeric materials of high strength and high modulus of elasticity have been developed. The polymeric materials are called engineering plastics, and generally defined as having such a performance that the heat deformation temperature is 100° C. or higher, the tensile strength is not less than 60 MPa, and the modulus of elasticity is not less than 2 GPa.

During the development of liquid-crystalline engineering plastics, the inventors of the present invention focused attention on 4-hydroxycinnamic acid (4HCA) as a reactive plant-derived rigid substance. Few researches existed on 4HCA homopolymer (poly-4HCA), and they were directed solely to the synthesis of the polymer, and polymer particles. The inventors of the present invention found for the first time that poly-4HCA as one of polyesters of natural origin has nematic liquid-crystalline properties. Poly-4HCA was photoreactive and biocompatible, and had the heat resistance as required of engineering plastics, but was brittle, and poor in solubility and processability. Such problems with the polymer were considered to be caused by a low molecular weight, and a high rigidity of the molecular backbone of the polymer.

With this being the situation, the inventors thought of copolymerization with a natural product imparting flexibility to the backbone of poly-4HCA, and focused on 3,4-dihydroxycinnamic acid (caffeic acid: DHCA) as a 4HCA derivative. In the presence of acetic anhydride as a transesterification agent and sodium acetate as a catalyst, 4HCA and DHCA were heated at 200° C. for six hours to polycondense them so as to obtain a DHCA-4HCA copolymer. The copolymer as obtained was solid at 25° C. in spite of DHCA contained in the copolymer. When, however, the copolymer was heated, a banding pattern was distinctly observed, that is to say, the copolymer exhibited its flowing property, so that it was confirmed that the copolymer was liquid crystal. The liquid crystallization temperature decreased to 150° C. in accordance with the increase in compositional ratio of DHCA, while the weight reduction temperature exceeded 300° C. As a consequence, the copolymer was easy to handle because of its enlarged temperature range of liquid crystallization (Non-Patent Literature 1).

In addition, the inventors of the present invention succeeded in increasing the molecular weight of a DHCA-4HCA copolymer that strongly influences the strength and the modulus of elasticity of the copolymer. To be more specific: When a compression test was conducted on the resultant DHCA-4HCA copolymer with respect to the strength and the modulus of elasticity, each varying with the compositional ratio of the copolymer, the test results showed that the copolymer was comparable to polycarbonate as a representative of engineering plastics for general purpose use in breaking strength and Young's modulus of elasticity if it contained 50 to 100 mol % DHCA (Patent Literature 1).

Hydrophilic block copolymers or graft copolymers generally form micelles in water through self-organization. It is known that the micelle as formed through self-organization has an internal hydrophobic core and external hydrophilic groups. The micelle-forming copolymer which is biocompatible is used as a sustained drug release material because the copolymer encapsulates a drug in the hydrophobic cores of its micelles, and improves the dispersibility of the drug in the blood by the action of the hydrophilic groups outside the core. The sustained drug release material as such is considered to carry a lot of potential for migration into the blood, and so forth if made nanoparticulate. The biocompatibility should refer to a property of suppressing non-specific adsorption of a substance of biological origin, such as protein, being non-cytotoxic, non-antigenic, and non-inflammatory, being stable in the blood or other body fluids, and so forth.

Nanoparticles are commonly sensitive to such external factors as temperature, pH, electromagnetic field, and light, whereupon those having an unsaturated bond are receiving special attention as the nanoparticles which are easily and quickly controllable in material properties as appropriate to individual uses because of their photoreactivity. For instance, researches have been conducted on various situations including the application of poly-4HCA or 4HCA copolymer because 4HCA and its derivatives having unsaturated bonds are known for their crosslinking polymerization by ultraviolet light.

The inventors of the present invention already succeeded in producing nanoparticles by causing the self-organization of poly-4HCA and DHCA homopolymer in a solvent. They demonstrated that the nanoparticles as produced were photoreactive, were hydrolyzed under alkaline conditions, and had an interesting variation in particle size. A problem with nanoparticles of DHCA-4HCA copolymers, however, still exists in that such nanoparticles are not applicable to a medical material such as drug delivery system due to their high hydrophobicity preventing them from being dispersed in an aqueous solution.

CITATION LIST

Patent Literature

Patent Literature 1: JP 2004-250700 A

Non-Patent Literature

Non-Patent Literature 1: Mitsuru AKASHI, "Kankyojunkan-gata Enjiniaringupurasuchikku (environmentally recyclable engineering plastics)," KOBUNSHI (High Polymers, Japan), the organ of The Society of Polymer Science, Japan, Vol. 55, No. 11, pp. 870-873, 2006.

SUMMARY OF INVENTION

Technical Problems

An object of the present invention is to provide a hydrophilic material, which is hydrophilic, biocompatible, and capable of being made nanoparticulate, and in which a hydrophilic monomer or polymer is attached to a polymer containing an aromatic compound, and more specifically, to provide a hydrophilic material with a nano-order particle size, which has a good dispersibility in water to readily migrate into the blood, and is useful as a drug carrier for drug delivery or the like.

Solution to Problems

In order to achieve the above object, the present invention provides the hydrophilic material as described in the following (1) through (14).

(1) A hydrophilic material, comprising a polymer containing an aromatic compound whose aromatic ring is substituted with an $\alpha,\beta$-unsaturated carboxy group and one or more hydroxy groups, wherein a hydrophilic monomer or a hydrophilic polymer is attached to the $\beta$ position of the $\alpha,\beta$-unsaturated carboxy group.

(2) The hydrophilic material according to (1) as above, wherein the aromatic compound is at least one cinnamic acid derivative selected from the group consisting of 2-hydroxycinnamic acid, 3-hydroxycinnamic acid, 4-hydroxycinnamic acid, 4-hydroxy-2-methoxycinnamic acid, 4-hydroxy-3-methoxycinnamic acid, and 3,4-dihydroxycinnamic acid.

(3) The hydrophilic material according to (1) as above, wherein the polymer containing an aromatic compound is a polyester copolymer containing 4-hydroxycinnamic acid and 3,4-dihydroxycinnamic acid.

(4) The hydrophilic material according to (1) as above, wherein the polymer containing an aromatic compound has a degree of polymerization of 10 to 10,000.

(5) The hydrophilic material according to (1) as above, wherein the hydrophilic monomer or the hydrophilic polymer is attached to the polymer containing an aromatic compound at an attachment rate of 1 to 100%.

(6) The hydrophilic material according to (1) as above, wherein the hydrophilic monomer is at least one monomer selected from the group consisting of alcohol, alkylene ether, a monomer having a sulfone group, a monomer having a carboxy group, a monomer having an amino group, and a monomer having a cyano group, and has at least one functional group to be attached to the $\beta$ position of the $\alpha,\beta$-unsaturated carboxy group.

(7) The hydrophilic material according to (6) as above, wherein the alcohol is at least one polyhydric alcohol selected from the group consisting of ethylene glycol, trimethylene glycol, glycerin, pentaerythritol, and threitol.

(8) The hydrophilic material according to (1) as above, wherein the hydrophilic polymer is at least one polymer selected from the group consisting of a polymer or copolymer of polyhydric alcohol, a polymer or copolymer of acrylic acid, a polymer or copolymer of methacrylic acid, and a polymer or copolymer of vinyl alcohol, and has at least one functional group to be attached to the $\beta$ position of the $\alpha,\beta$-unsaturated carboxy group.

(9) The hydrophilic material according to (8) as above, wherein the polymer of polyhydric alcohol is at least one polyalkylene glycol selected from the group consisting of polyethylene glycol, polypropylene glycol, and polyethylene-propylene glycol, and has at least one group reactive with the polymer containing an aromatic compound.

(10) The hydrophilic material according to (8) as above, wherein the hydrophilic polymer has a degree of polymerization of 10 to 20,000.

(11) The hydrophilic material according to (1) as above, wherein the hydrophilic monomer or the hydrophilic polymer is attached to the $\beta$ position of the $\alpha,\beta$-unsaturated carboxy group through a sulfur atom or an oxygen atom.

(12) The hydrophilic material according to (1) as above, which is in a nanoparticulate form.

(13) A medical material, having the hydrophilic material according to any one of (1) through (12) as above used therein.

(14) A sustained drug release material, having the hydrophilic material according to any one of (1) through (12) as above used therein.

Advantageous Effects of Invention

The hydrophilic material of the present invention is a novel compound.

The hydrophilic material of the present invention is hydrophilic, biocompatible, and capable of being made nanoparticulate, so that it has a good dispersibility in water to readily migrate into the blood, and is useful as a drug carrier for drug delivery or the like.

BRIEF DESCRIPTION OF DRAWINGS

FIG. 1 shows $^1$H NMR spectra of the hydrophilic material (PCA-DTT) in which threitol is attached to a 3,4-dihydroxycinnamic acid-4-hydroxycinnamic acid copolymer (six specimens): (A) shows the structural formula from which the atoms or atomic groups as sources of nuclear magnetic resonance are seen, and (B) shows the $^1$H NMR spectra.

FIG. 5 shows UV irradiation-induced changes of the particulate, hydrophilic material (PCA-DTT) in which threitol is attached to a 3,4-dihydroxycinnamic acid-4-hydroxycinnamic acid copolymer (six specimens): (A) illustrates the mechanism of the reaction caused by UV irradiation, (B) shows $^1$H NMR absorption spectra before and after UV irradiation, (C) is a graph showing the variation in absorption intensity with irradiation time, and (D) is a graph showing the relationship between the UV irradiation time and the absorption intensity for the individual specimens having different DTT attachment rates.

FIG. 6 shows the UV irradiation-induced change in particle size of the particulate, hydrophilic material (PCA-DTT) in which threitol is attached to a 3,4-dihydroxycinnamic acid-4-hydroxycinnamic acid copolymer (six specimens): (A) is a graph showing the percent reduction in particle size of the individual specimens having different DTT attachment rates, and (B) is a schematic diagram illustrating the UV irradiation-induced change in particle size.

FIG. 8 shows the change in particle size of the particulate, hydrophilic material (PCA-DTT) in which threitol is attached to a 3,4-dihydroxycinnamic acid-4-hydroxycinnamic acid copolymer (six specimens), as a result of carrying BSA: (A) is a graph showing the relationship between the DTT attachment rate and the particle size of the PCA-DTT, (B) is an SEM image of the particles before carrying BSA, and (C) is an SEM image of the particles after carrying BSA.

FIG. 9 shows the sustained BSA release behavior of the particulate, hydrophilic material (PCA-DTT) in which threitol is attached to a 3,4-dihydroxycinnamic acid-4-hydroxycinnamic acid copolymer (six specimens): (A) is a graph showing the relationship between the sustained BSA release time and the amount of BSA sustainedly released, and (B) is a schematic diagram illustrating the change in particle size with different pH values.

FIG. 10 shows the sustained BSA release behavior of the particulate, hydrophilic material (PCA-DTT-11) in which threitol is attached to a 3,4-dihydroxycinnamic acid-4-hydroxycinnamic acid copolymer, before and after crosslinkage: (A) is a graph showing the relationship between the sustained BSA release time and the amount of BSA sustainedly released, and (B) is a schematic diagram illustrating the change in particle size caused by crosslinkage.

DESCRIPTION OF EMBODIMENTS

The hydrophilic material of the present invention is the hydrophilic material in which, to a polymer (including copolymer) containing a polymeric unit derived from the aromatic compound whose aromatic ring is substituted with an $\alpha,\beta$-unsaturated carboxy group and one or more hydroxy groups (hereafter also referred to simply as "polymer containing an aromatic compound"), a hydrophilic monomer or a hydrophilic polymer (including copolymer) having a functional group capable of being attached to the $\beta$ position of the $\alpha,\beta$-unsaturated carboxy group (such a polymer being hereafter also referred to simply as "hydrophilic polymer") is attached.

The polymer containing an aromatic compound that constitutes the backbone of the hydrophilic material of the present invention is not particularly limited, while an aromatic polyester obtained by polycondensation of the $\alpha,\beta$-unsaturated carboxy group and the hydroxy group as substituents on the aromatic ring is preferable from the viewpoint of biocompatibility, with an aromatic polyester copolymer composed of two kinds of aromatic compounds being more preferable.

The degree of polymerization of the polymer containing an aromatic compound as the backbone is not particularly limited within the range of 10 to 10,000, and is preferably 50 to 8,000, more preferably 100 to 6,000, irrespective of the type of the polymer, which may be a homopolymer, a random copolymer, or a block copolymer. In the case of copolymer, the molar ratio between aromatic compounds is not particularly limited.

The hydrophilic material tends to have a larger particle size and a narrower particle size distribution, and be more convenient to use as a sustained drug release material, as the degree of polymerization of the polymer containing an aromatic compound as the backbone is higher.

The aromatic compound is not particularly limited as long as its aromatic ring is substituted with an $\alpha,\beta$-unsaturated carboxy group and one or more hydroxy groups, while a derivative of cinnamic acid or allocinnamic acid is preferable. Examples of the cinnamic acid derivative include 2-hydroxycinnamic acid, 3-hydroxycinnamic acid, 4-hydroxycinnamic acid (4HCA), 4-hydroxy-2-methoxycinnamic acid, 4-hydroxy-3-methoxycinnamic acid, and 3,4-dihydroxycinnamic acid (DHCA). Typical allocinnamic acid derivatives are analogous to the exemplary cinnamic acid derivatives as above. More preferable are 4HCA, DHCA, and the like, with 4HCA and DHCA used in combination being especially preferred.

The polymer containing an aromatic compound may be obtained by, for instance, heating 4HCA and DHCA in the presence of acetic anhydride as a catalyst and sodium acetate as a transesterification agent under shading in a nitrogen atmosphere so as to polycondense them into a DHCA-4HCA copolymer, and extracting and purifying the resultant copolymer.

The hydrophilic monomer or hydrophilic polymer to be attached to the polymer containing an aromatic compound needs to have a functional group capable of being attached to the $\beta$ position of the $\alpha,\beta$-unsaturated carboxy group of the polymer containing an aromatic compound, and preferably has a mercapto group, a hydroxy group, or the like which facilitates the attachment to the $\beta$ position, especially a mercapto group.

The hydrophilic monomer is not particularly limited as long as it is the alcohol, alkylene ether, monomer having a sulfone group, monomer having a carboxy group, monomer having an amino group, monomer having a cyano group, monomer having a mercapto group, or the like which has at least one functional group capable of being attached to the $\beta$ position of the $\alpha,\beta$-unsaturated carboxy group of the polymer containing an aromatic compound. From the viewpoint of biocompatibility, the hydrophilic monomer is preferably alcohol, and an alcohol thiolated at an end hydroxy group is favorable because of its reactivity. It is also possible to use two or more kinds of hydrophilic monomers in combination.

The preferred alcohol is polyhydric alcohol, which is exemplified by those with low molecular weights, including ethylene glycol, trimethylene glycol, glycerin, pentaerythritol, and threitol. A polyhydric alcohol thiolated at an end hydroxy group such as dithiothreitol may be used. It is also possible to use two or more kinds of polyhydric alcohols in combination.

The hydrophilic polymer is not particularly limited as long as it is the polymer or copolymer of polyhydric alcohol, polymer or copolymer of acrylic acid, polymer or copolymer of methacrylic acid, polymer or copolymer of vinyl alcohol, or other polymer which has at least one functional group capable of being attached to the $\beta$ position of the $\alpha,\beta$-unsaturated carboxy group of the polymer containing an aromatic compound. From the viewpoint of biocompatibility, a polymer of polyhydric alcohol is particularly preferred. A polymer of a polyhydric alcohol thiolated at an end hydroxy group is favorable because of its reactivity. It is also possible to use two or more kinds of hydrophilic polymers in combination.

Examples of the polymer of polyhydric alcohol include polyalkylene glycol, such as polyethylene glycol, polypropylene glycol, and polyethylene-propylene glycol. It is also possible to use two or more kinds of polyhydric alcohols in combination. The functional group at the other end of the hydrophilic polymer is preferably masked by a methyl group or the like.

The degree of polymerization of the hydrophilic polymer is 2 to 20,000, preferably 3 to 15,000, and more preferably 4 to 10,000. The hydrophilic material tends to have a larger particle size and a narrower particle size distribution, with its dispersibility in water being improved and, accordingly, its usability being generally enhanced, as the degree of polymerization of the hydrophilic polymer is higher. Therefore, if the hydrophilic material is to be used as a medical material, a hydrophilic polymer with a higher degree of polymerization is more preferable.

If a hydrophilic monomer is to be used, the hydrophilic material may be produced by, for instance, adding an end-thiolated threitol, such as dithiothreitol, as a hydrophilic monomer to a polymer containing an aromatic compound to heat them in the presence of an amine catalyst. If a hydrophilic polymer is to be used, the hydrophilic material may similarly be produced by, for instance, adding an end-thiolated polyethylene glycol as a hydrophilic polymer to a polymer containing an aromatic compound to heat them in the presence of an amine catalyst.

The hydrophilic material in which the hydrophilic monomer or polymer molecules as attached to the β positions of α,β-unsaturated carboxy groups of the polymer containing an aromatic compound are higher in number, that is to say, the hydrophilic material which has a higher rate of hydrophilic monomer or polymer attachment, tends to have a larger particle size and a narrower particle size distribution, with its dispersibility in water being improved and its usability being enhanced. Therefore, if the hydrophilic material is to be used as a medical material, the hydrophilic monomer or polymer attachment rate thereof is more preferable as it is higher.

The hydrophilic material of the present invention is typically the hydrophilic material in which polyethylene glycol is attached to a DHCA-4HCA copolymer (PCA), as represented by Structural Formula (1) below.

[Chemical Formula 1]

(1)

In Formula (1), m is 10 to 10,000, n is 10 to 10,000, and p is 2 to 20,000, while m is preferably 50 to 8,000, more preferably 100 to 6,000, and n is preferably 50 to 8,000, more preferably 100 to 6,000. In addition, p is preferably 3 to 15,000, more preferably 4 to 10,000.

The hydrophilic material as represented by Formula (1) generally has a number-average molecular weight (Mn) of 1,000 to 1,000,000, preferably of 1,100 to 100,000, as varying with application, whereupon the molecular weight distribution, namely the ratio (Mw/Mn) of the weight-average molecular weight (Mw) to the number-average molecular weight, is preferably 1.01 to 10.00, more preferably 1.01 to 7.00.

As another typical example of the hydrophilic material of the present invention, the hydrophilic material as represented by Structural Formula (2) below, which has threitol attached to a DHCA-4HCA copolymer (PCA), and is crosslinked, may be mentioned.

[Chemical Formula 2]

(2)

In Structural Formula (2), m is 10 to 10,000, and n is 10 to 10,000, while m and n are each preferably 50 to 8,000, more preferably 100 to 6,000.

The hydrophilic material as represented by Formula (2) generally has a molecular weight Mn of 1,000 to 1,000,000, preferably of 1,100 to 100,000, as varying with application, whereupon the ratio Mw/Mn is 1.01 to 10.00, preferably 1.01 to 7.00.

The hydrophilic material of the present invention is not particularly limited in particle shape, while particles of the material are preferably spherical in shape.

The hydrophilic material of the present invention has a particle size of 10 to 20,000 nm, preferably of 15 to 10,000 nm, more preferably of 20 to 10,000 nm. While it goes without saying that the particle size of the hydrophilic material varies with the degree of polymerization of the polymer containing an aromatic compound, the amount of the hydrophilic monomer or polymer as attached, the degree of polymerization of the hydrophilic polymer, and so forth, the ratio Mw/Mn is reduced as the degree of polymerization of the hydrophilic material, namely the molecular weight Mn thereof, is increased, which leads to a narrower particle size distribution.

The hydrophilic material of the present invention is biocompatible, which specifically means that, when fibroblasts were seeded on the surface of the hydrophilic material, and the cell adhesion number was measured, it was found that almost no cells were adhered to the surface.

The hydrophilic material of the present invention is excellent in mechanical strength, flexibility, photoreactivity, hydrophilicity and biocompatibility, and ready to make particulate, so that it is available for a variety of applications of a hydrophilic material. Specifically, the hydrophilic material is suitable for medical use, especially for the use as a sustained drug release material.

EXAMPLES

The present invention is illustrated in reference to the following examples, to which the present invention is in no way limited.

Example 1

Hydrophilic material (PCA-DTT) having threitol attached to a 3,4-dihydroxycinnamic acid (DHCA)-4-hydroxycinnamic acid (4HCA) copolymer (PCA).

In a three-neck flask, 5.40 g of 3,4-dihydroxycinnamic acid (DHCA: caffeic acid), 4.90 g of 4-hydroxycinnamic acid (4HCA), 0.05 g of sodium acetate as a catalyst, and 50 mL of acetic anhydride as a transesterification agent were subjected to nitrogen bubbling for 10 minutes, then the flask was placed in an oil bath at 200° C. for six hours under a nitrogen flow to cause polycondensation.

The resultant precipitation was dissolved in dimethylformamide, and reprecipitated in methanol. After suction filtration, the precipitation was vacuum dried at room temperature for a whole day and night to obtain a DHCA-4HCA copolymer (PCA) with a molecular weight Mw of 25,000 and a 1:1 molar ratio of DHCA to 4HCA. The molar ratio was calculated from $^1$H NMR absorption spectra obtained using a nuclear magnetic resonance instrument (UNITY 400 Plus manufactured by Varian, Inc.).

To the PCA as above, dithiothreitol (DTT) was added at the ratios as set forth in Table 1 below, and triethylamine as a catalyst was added dropwise, then the mixtures were agitated at 60° C. for 12 hours so as to attach DTT to the PCA to prepare hydrophilic materials (PCA-DTTs) (see the chemical formula (3)). The yields (mol %) of the individual PCA-DTTs (six specimens) are set forth in Table 1.

The DTT attachment rate was calculated from the $^1$H NMR absorption spectra (FIG. 1) as obtained using a nuclear magnetic resonance instrument (UNITY 400 Plus manufactured by Varian, Inc.), and by means of a UV-VIS spectrophotometer. The DTT attachment rate values (mol %) as calculated are set forth in Table 1.

Figure 1A:
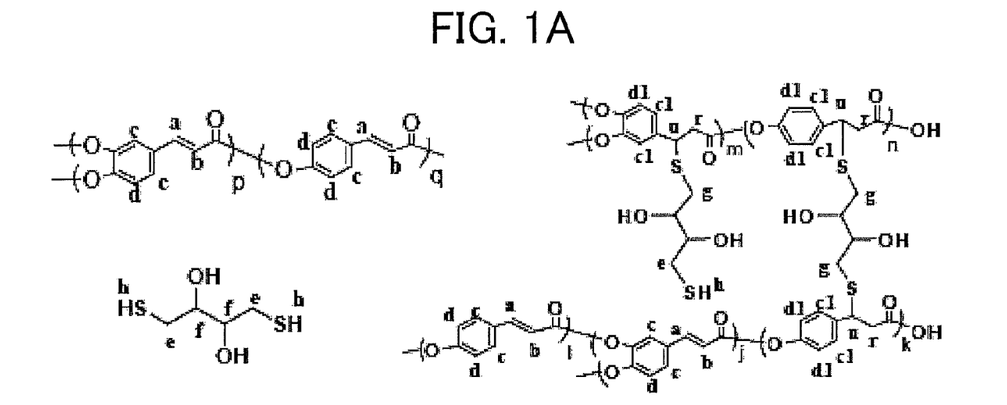
Figure 1B:
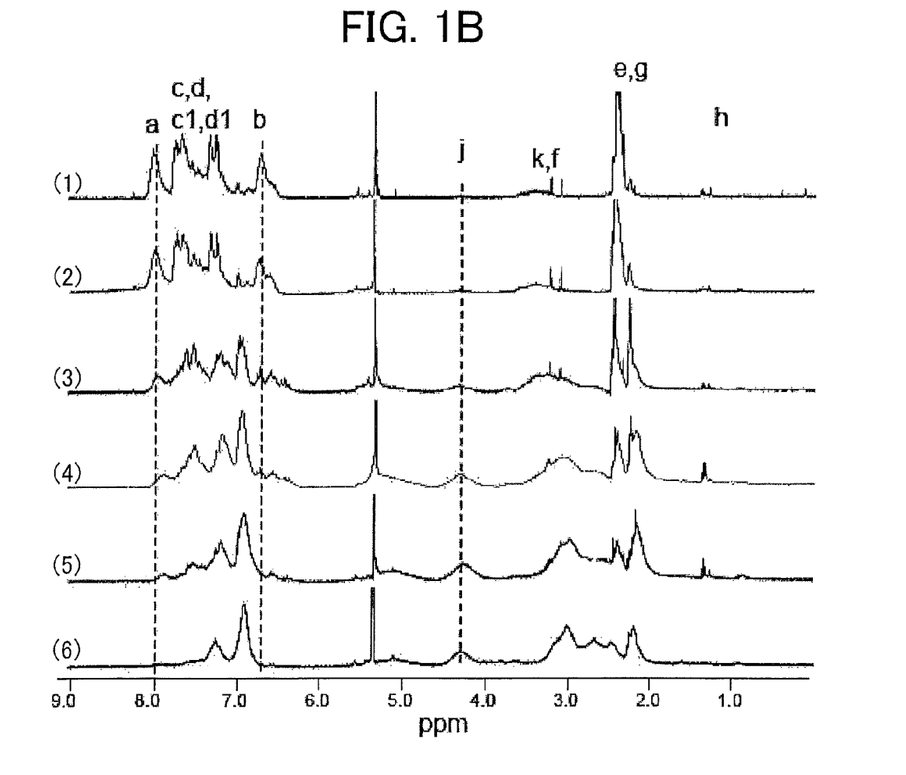

The atoms or atomic groups of the compounds that correspond to the absorption peaks (a, c, c1, d1, b, j, k, f, e, g, and h) of the individual PCA-DTTs as shown in FIG. 1B, respectively, are shown in FIG. 1A.

In Table 1, the term "raw material" means the mole ratio of DTT fed to the total mole ratio of 4HCA and thiol groups, the term "from $^1$H NMR" means the DTT attachment rate value as calculated from a $^1$H NMR absorption spectrum, and the term "from UV-VIS" means the DTT attachment rate value as calculated from a UV-VIS spectrum.

When fibroblasts were seeded on the surface of each PCA-DTT, almost no cells were adhered to the relevant surface, which has demonstrated that the hydrophilic material is biocompatible.

[Chemical Formula 3]

TABLE 1

| No. | Specimen | PCA (g) | DTT (mg) | Yield (%) | Hydrophilic Material | | | Particle size (nm) | Degree of dispersion (%) |
| --- | --- | --- | --- | --- | --- | --- | --- | --- | --- |
| | | | | | | DTT attachment rate (mol %) | | | |
| | | | | | Raw material | From $^1$H NMR | From UV-VIS | | |
| 1 | PCA-DTT-4 | 2 | 91 | 63 | 10 | 4 | 5 | 68 | 41.3 |
| 2 | PCA-DTT-11 | 2 | 181 | 86 | 20 | 11 | 11 | 97 | 38.5 |
| 3 | PCA-DTT-36 | 2 | 272 | 84 | 50 | 36 | 35 | 135 | 30.4 |
| 4 | PCA-DTT-56 | 2 | 363 | 73 | 80 | 56 | 50 | 178 | 22.4 |
| 5 | PCA-DTT-78 | 2 | 544 | 70 | 90 | 78 | 75 | 265 | 24.9 |
| 6 | PCA-DTT-98 | 2 | 1000 | 65 | 100 | 98 | 94 | 330 | 26.2 |

PCA-DTT particles (six specimens) were prepared by subjecting the individual PCA-DTTs (six specimens) to dissolution in dimethyl sulfoxide (DMSO), and dialysis in water for four days.

Figure 2:
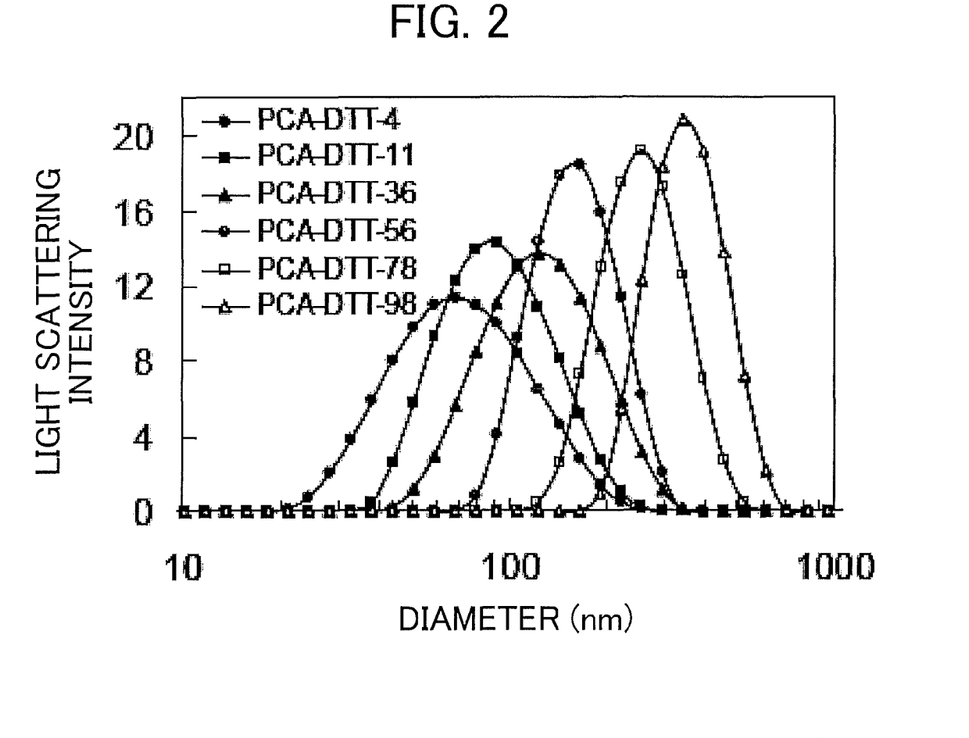
FIG. 2 is a graph showing the relationship between the particle size and the light scattering intensity (degree of dispersion) of the particulate, hydrophilic material (PCA-DTT) in which threitol is attached to a 3,4-dihydroxycinnamic acid-4-hydroxycinnamic acid copolymer (six specimens).

By a dynamic light scattering method using a dynamic light scattering instrument (Zetasizer Nano ZS manufactured by Malvern Instruments Ltd), the particle size and the degree of dispersion (standard deviation/mean particle size) of each particulate PCA-DTT were found. The results are set forth in Table 1. It was confirmed that the particles of any PCA-DTT were nanoparticles. The individual particulate PCA-DTTs (six specimens) are shown in the graph on which the particle size is plotted on the x-axis, and the light scattering intensity on the y-axis (FIG. 2).

Figure 3:
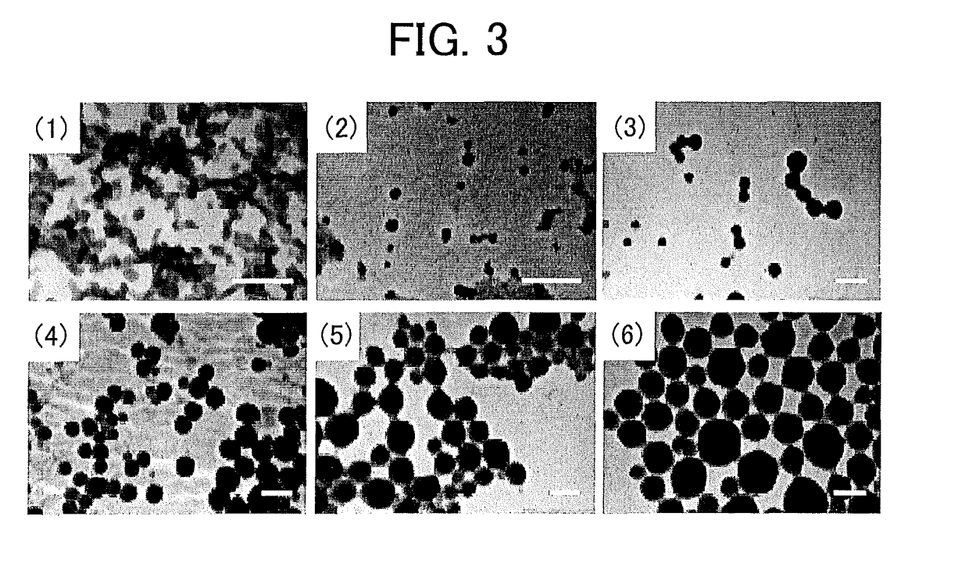
FIG. 3 shows TEM images of the particulate, hydrophilic material (PCA-DTT) in which threitol is attached to a 3,4-dihydroxycinnamic acid-4-hydroxycinnamic acid copolymer (six specimens).
Figure 4:
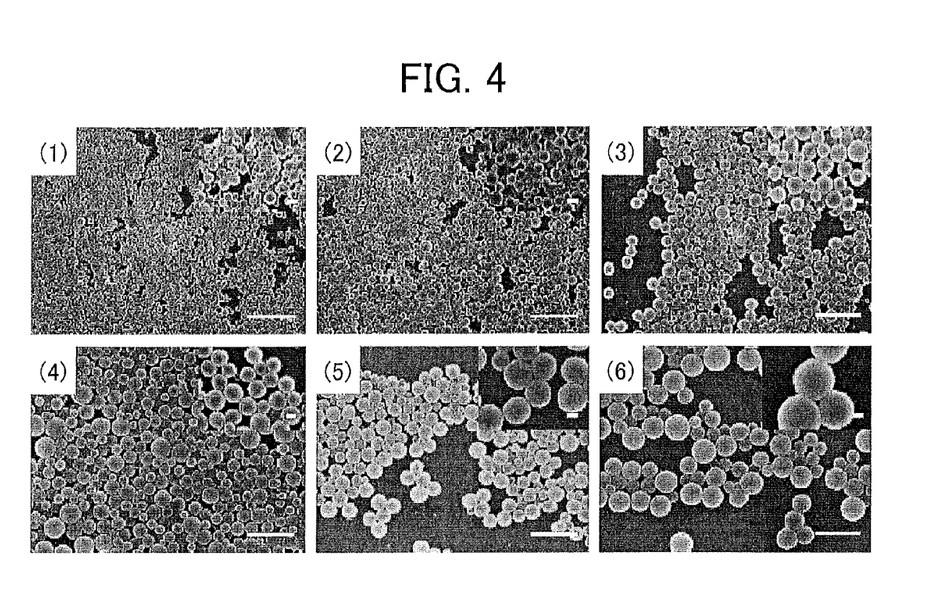
FIG. 4 shows SEM images of the particulate, hydrophilic material (PCA-DTT) in which threitol is attached to a 3,4-dihydroxycinnamic acid-4-hydroxycinnamic acid copolymer (six specimens).
Figure 5A:
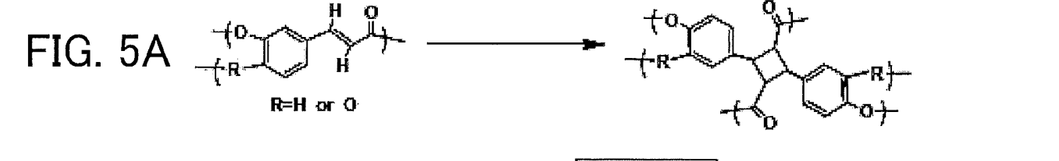
Figure 5B:
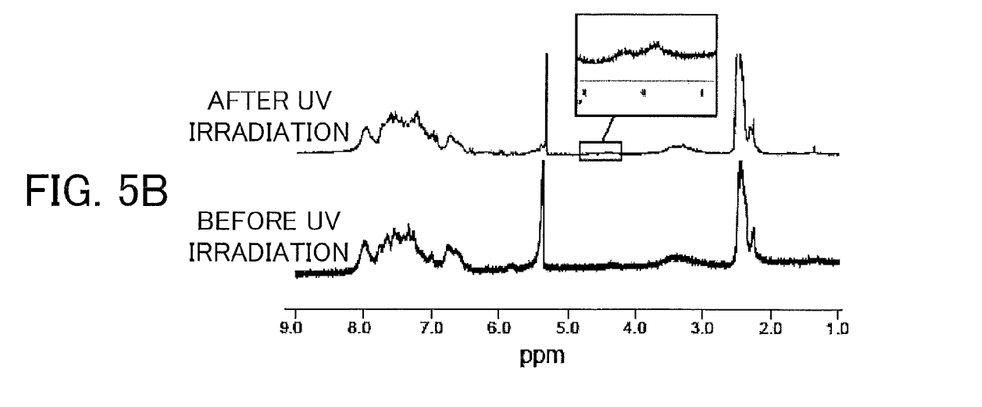
Figure 5C:
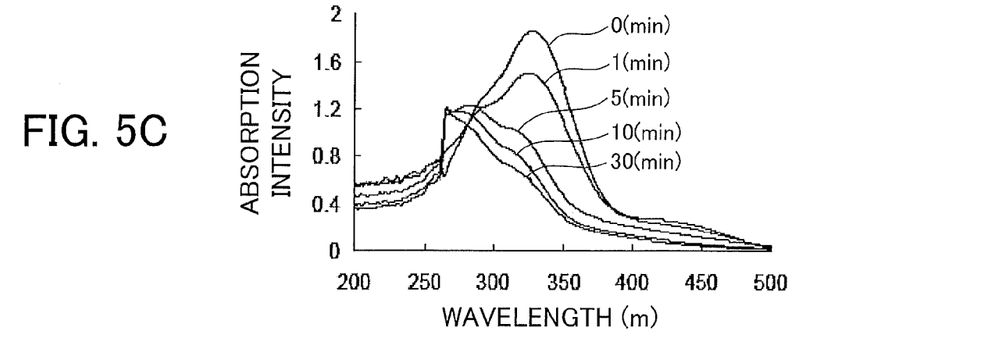
Figure 5D:
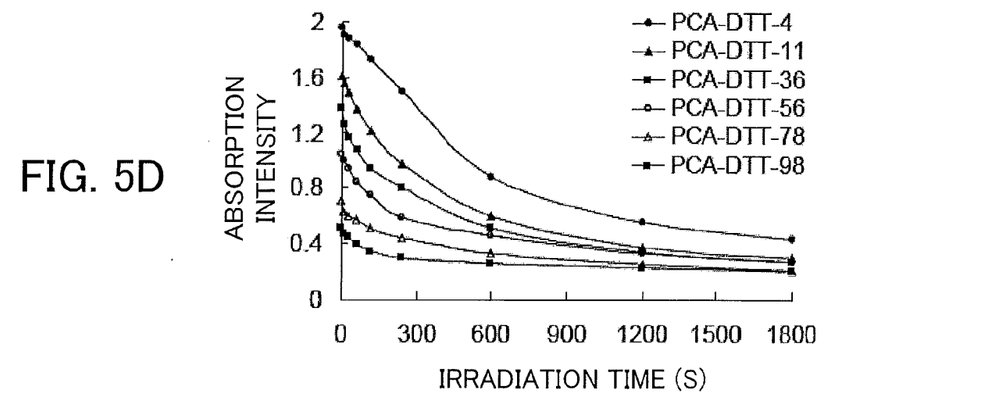

The particulate PCA-DTTs (6 specimens) are also shown in TEM images (FIG. 3) and SEM images (FIG. 4). In FIGS. 3 and 4, the numbers (1) through (6) correspond to the numbers 1 through 6 in Table 1, respectively, that is to say, denote the specimens PCA-DTT-4 through PCA-DTT-98, respectively.

As evident from Table 1 and FIGS. 1 through 4, as the DTT molecules as attached to the β positions of the α,β-unsaturated carboxy groups of PCA were increased in number, that is to say, the DTT attachment rate was increased to 11%, 36%, or even 56%, 78%, or 98%, the particle size was increased, and presented a narrower particle size distribution of a monodisperse type (lower degree of dispersion), indicating a better dispersibility in water (hydrophilicity).

The individual particulate PCA-DTTs were subjected to UV irradiation, and examined by a UV-VIS spectrophotometer on the reduction in intensity of the absorption caused by unsaturated bonds (FIG. 5). By UV irradiation, the addition reaction as shown in FIG. 5A occurred, and the spectral change as shown in FIG. 5B was observed. As a consequence, the absorption at wavelengths near 320 to 330 nm that is caused by C=C bonds was reduced in intensity as the irradiation time was increased (FIG. 5C). The particulate PCA-DTT whose DTT content was higher had a lower photoreactivity (FIG. 5D).

Figure 6A:
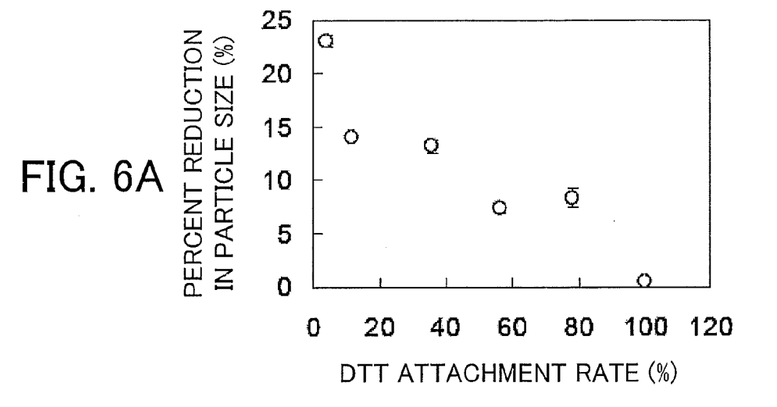
Figure 6B:
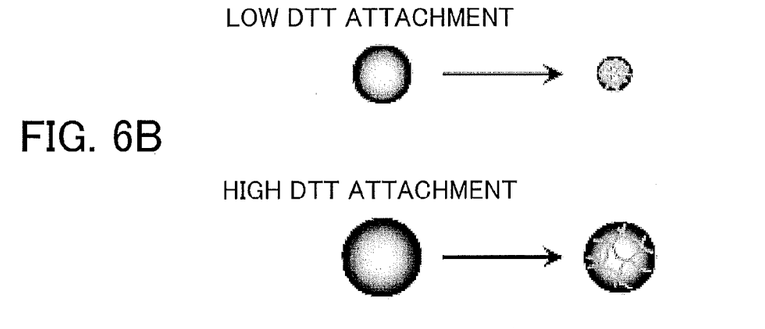

During the UV irradiation, the particulate PCA-DTTs were reduced over time in particle size (FIG. 6A), and it was found that the particle size of the particulate PCA-DTTs was made compact (FIG. 6B).

The individual particulate PCA-DTTs were also examined on the property of sustainedly releasing a drug. Each particulate PCA-DTT was dissolved in DMSO at a concentration of 10 mg/ml, and fluorescein isothiocyanate (FITC)-labeled bovine serum albumin (FITC-BSA) was dissolved in phosphate buffered saline (PBS: pH 7.4) at a concentration of 2 mg/ml. The FITC-BSA solution was added dropwise to the solution of particulate PCA-DTT in DMSO to prepare particles with BSA encapsulated therein. The resultant particles were collected by centrifugation, and washed with ultrapure water three Limes. The amount of the BSA as carried by the particles was determined from the fluorescence intensity of the carried FITC-BSA using a fluorescence spectrum instrument (Wallac 1420 ARVO manufactured by PerkinElmer Inc.). The particle size of the particles with BSA encapsulated therein was evaluated by a dynamic scattering method and SEM observation.

Figure 7:
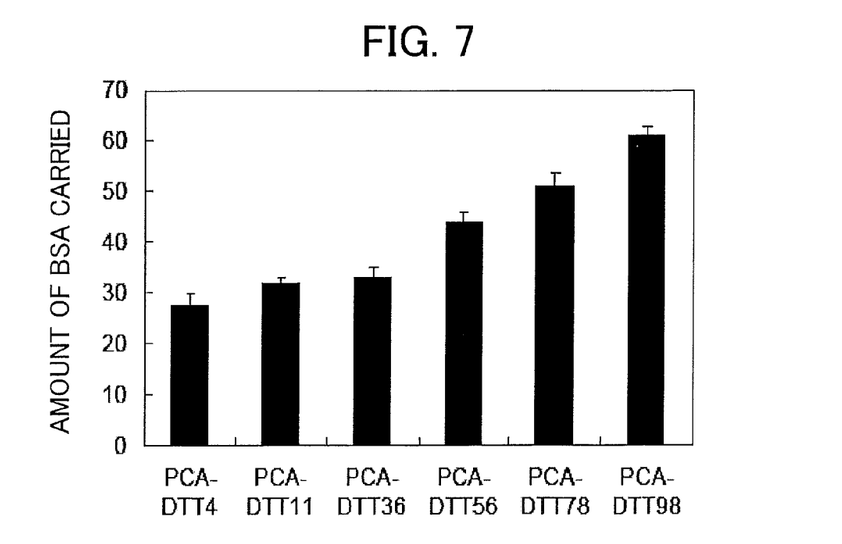
FIG. 7 is a graph showing amounts (μg/mg) of BSA carried by the hydrophilic material (PCA-DTT) in which threitol is attached to a 3,4-dihydroxycinnamic acid-4-hydroxycinnamic acid copolymer (six specimens).
Figure 8A:
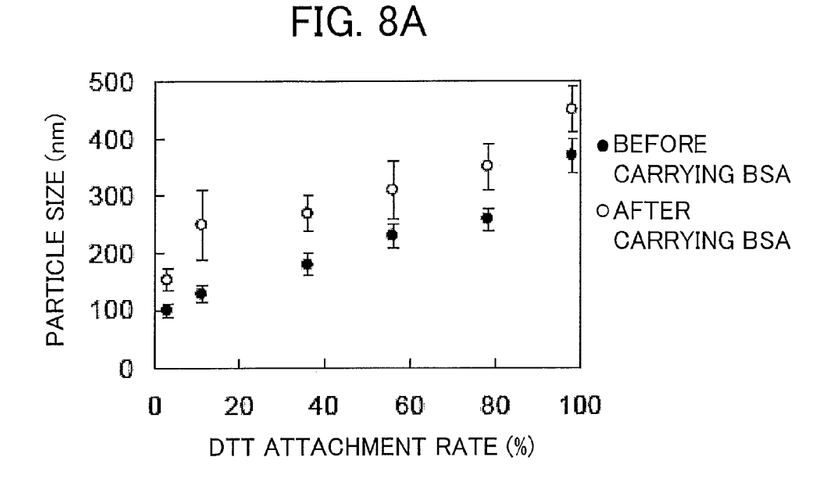
Figure 8B:
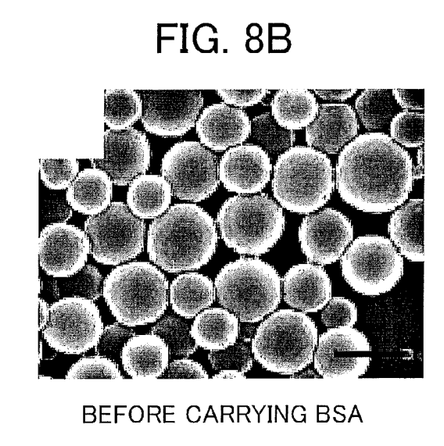
Figure 8C:
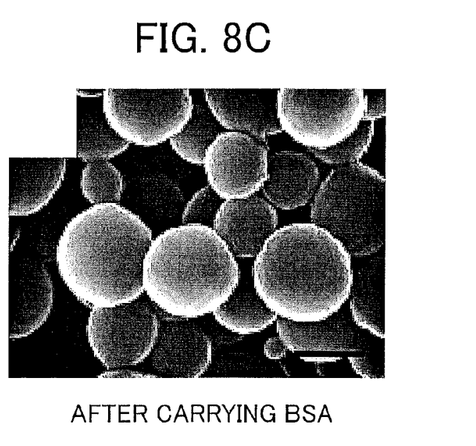

The results showed that the amount of the BSA as carried was increased as the DTT attachment rate was increased (FIG. 7). In addition, it was found that the particle size was increased as the DTT attachment rate was increased (FIG. 8A), and it was seen from SEM images of the particles before and after carrying BSA that the particles after carrying BSA had enlarged particle sizes considered as a result of the encapsulation of BSA (FIGS. 8B and 8C).

Finally, a particulate PCA-DTT with BSA encapsulated therein was evaluated on its property of sustainedly releasing BSA. The particulate PCA-DTT-11 with BSA encapsulated therein was immersed in buffer solutions of different pH values, then the solutions were agitated over a specified period of time, and the amount of BSA sustainedly released was evaluated by measuring the fluorescence intensity of supernatants over time. On the other hand, the particulate PCA-DTT-11 with BSA encapsulated therein that was photocrosslinked was immersed in a buffer solution of pH 7.4, and the amount of BSA sustainedly released was evaluated in a similar manner to the above.

Figure 9A:
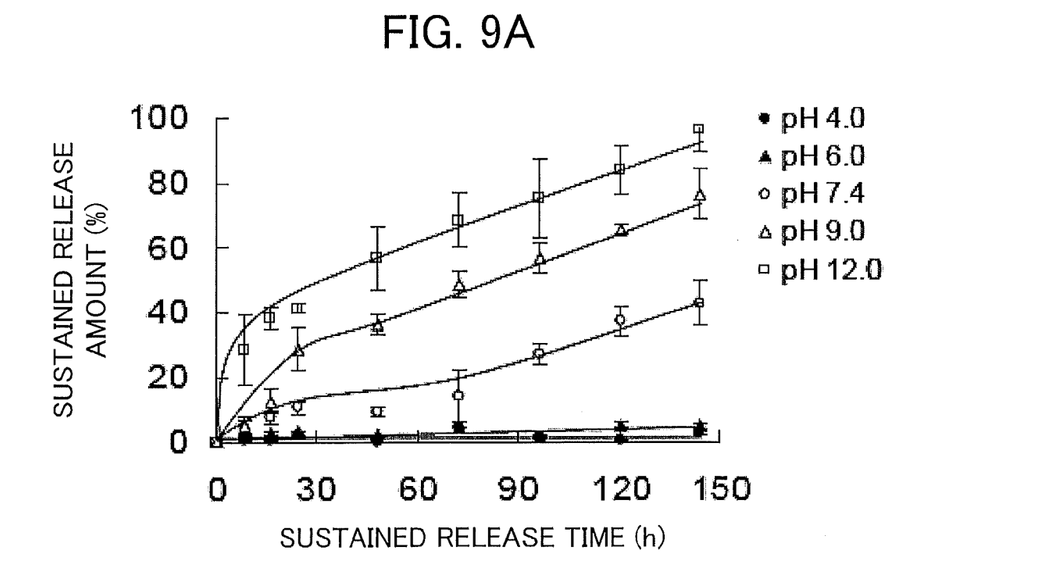
Figure 9B:
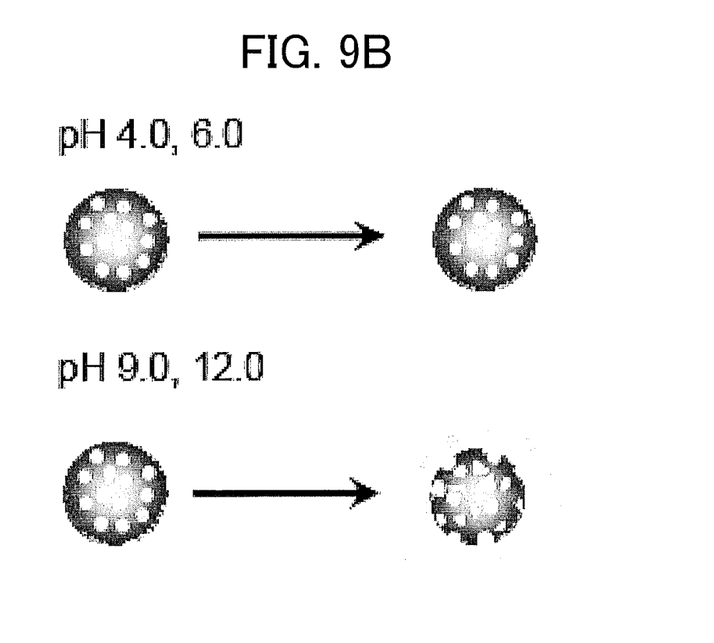

The results showed that, while almost no BSA was released even after a lapse of 150 hours in acidic buffer solutions, BSA was sustainedly released in a neutral or alkaline buffer solution, in a larger amount in a more alkaline solution, owing to the decomposition of particles (FIGS. 9A and 9B).

Figure 10A:
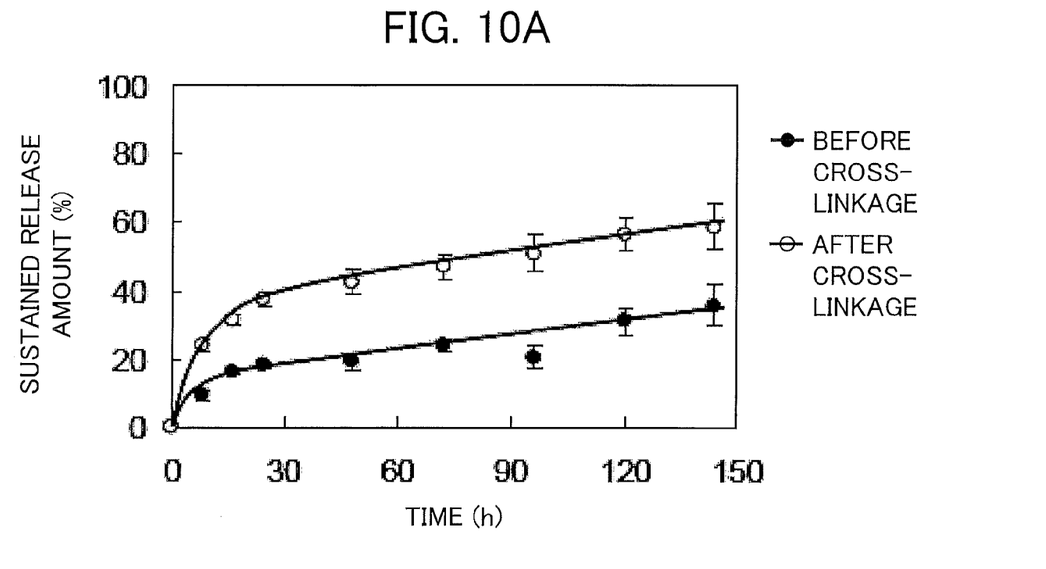
Figure 10B:
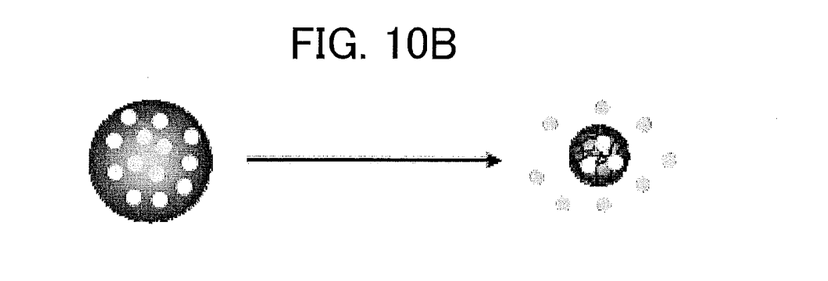

In the buffer solution which had a pH value close to that in the living body, 7.4, the particulate PCA-DTT as photocrosslinked released BSA faster than before the crosslinkage (FIG. 10A), which indicated that the speed of sustained release can be controlled by the photocrosslinkage. A faster drug release appears to be caused by a reaction of molecules with one another upon crosslinkage leading to a compactor particle size (FIG. 10B).

Comparative Example 1

4-Hydroxycinnamic acid homopolymer (poly-4HCA)

In a three-neck flask, 9.85 g of 4-hydroxycinnamic acid (4HCA), 0.05 g of sodium acetate as a catalyst, and 50 mL of acetic anhydride as a transesterification agent were subjected to nitrogen bubbling for 10 minutes, then the flask was placed in an oil bath at 200° C. for six hours under a nitrogen flow to cause polycondensation with agitation. The resultant precipitation was dissolved in 100 mL of dimethylformamide, and reprecipitated in 1 L of methanol. After suction filtration, the precipitation was vacuum dried at room temperature for two whole days and nights to obtain poly-4HCA.

It was attempted to dissolve the poly-4HCA in DMSO so as to subject it to dialysis in water for four days to find the particle size and the degree of dispersion of the poly-4HCA by a dynamic light scattering method using a dynamic light scattering instrument (Zetasizer Nano ZS manufactured by Malvern Instruments Ltd), but the polymer was not dissolved in DMSO and, accordingly, could not be subjected to dialysis.

Comparative Example 2

3,4-Dihydroxycinnamic acid homopolymer (poly-DHCA)

In a three-neck flask, 10.93 g of 3,4-dihydroxycinnamic acid (DHCA), 0.05 g of sodium acetate as a catalyst, and 50 mL of acetic anhydride as a transesterification agent were subjected to nitrogen bubbling for 10 minutes, then the flask was placed in an oil bath at 200° C. for six hours under a nitrogen flow to cause polycondensation with agitation. The resultant precipitation was dissolved in 100 mL of dimethylformamide, and reprecipitated in 1 L of methanol. After suction filtration, the precipitation was vacuum dried at room temperature for two whole days and nights to obtain poly-DHCA.

It was attempted to dissolve the poly-DHCA in DMSO so as to subject it to dialysis in water for four days to find the particle size and the degree of dispersion of the poly-DHCA by a dynamic light scattering method using a dynamic light scattering instrument (Zetasizer Nano ZS manufactured by Malvern Instruments Ltd), but the polymer was not dissolved in DMSO and, accordingly, could not be subjected to dialysis.

LEGENDS

In FIGS. 1B, 3 and 4:
(1) denotes PCA-DTT-4;
(2) denotes PCA-DTT-11;
(3) denotes PCA-DTT-36;
(4) denotes PCA-DTT-56;
(5) denotes PCA-DTT-78; and
(6) denotes PCA-DTT-98.

The invention claimed is:

1. A hydrophilic material, comprising a polymer containing an aromatic compound whose aromatic ring is substituted with an $\alpha,\beta$-unsaturated carboxy group and one or more hydroxy groups, wherein dithiothreitol is attached to the $\beta$ position of the $\alpha,\beta$-unsaturated carboxy group, and wherein the dithiothreitol is attached to the polymer containing an aromatic compound at an attachment rate of 56 to 98 mol %.

2. The hydrophilic material according to claim 1, wherein the aromatic compound is at least one cinnamic acid derivative selected from the group consisting of 2-hydroxycinnamic acid, 3-hydroxycinnamic acid, 4-hydroxycinnamic acid, 4-hydroxy-2-methoxycinnamic acid, 4-hydroxy-3-methoxycinnamic acid, and 3,4-dihydroxycinnamic acid.

3. The hydrophilic material according to claim 1, wherein the polymer containing an aromatic compound is a polyester copolymer containing 4-hydroxycinnamic acid and 3,4-dihydroxycinnamic acid.

4. The hydrophilic material according to claim 1, wherein the polymer containing an aromatic compound has a degree of polymerization of 10 to 10,000.

5. The hydrophilic material according to claim 1, wherein the dithiothreitol is attached to the $\beta$ position of said $\alpha,\beta$-unsaturated carboxy group through a sulfur atom or an oxygen atom.

6. The hydrophilic material according to claim 1, which is in a nanoparticulate form.

7. A medical material, formed from at least the hydrophilic material according to claim 1.

8. A sustained drug release material, formed from at least the hydrophilic material according to claim 1.

* * * * *

UNITED STATES PATENT AND TRADEMARK OFFICE
CERTIFICATE OF CORRECTION

PATENT NO. : 8,835,570 B2  
APPLICATION NO. : 13/121604  
DATED : September 16, 2014  
INVENTOR(S) : Mitsuru Akashi et al.

Page 1 of 1

It is certified that error appears in the above-identified patent and that said Letters Patent is hereby corrected as shown below:

Title Page, item (75) Inventors:

Makoto Onishi: Change "Kanagawa" to -- Shizuoka --

Signed and Sealed this  
Twelfth Day of May, 2015

Michelle K. Lee  
*Director of the United States Patent and Trademark Office*